US008818300B2

(12) United States Patent
Falck et al.

(10) Patent No.: US 8,818,300 B2
(45) Date of Patent: Aug. 26, 2014

(54) COMBINING BODY-COUPLED COMMUNICATION AND RADIO FREQUENCY COMMUNICATION

(75) Inventors: Thomas Falck, Eindhoven (NL); Steven Corroy, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 547 days.

(21) Appl. No.: 13/141,705

(22) PCT Filed: Dec. 15, 2009

(86) PCT No.: PCT/IB2009/055752
§ 371 (c)(1),
(2), (4) Date: Jun. 23, 2011

(87) PCT Pub. No.: WO2010/073180
PCT Pub. Date: Jul. 1, 2010

(65) Prior Publication Data
US 2011/0269414 A1    Nov. 3, 2011

(30) Foreign Application Priority Data

Dec. 23, 2008   (EP) ..................................... 08306009

(51) Int. Cl.
*H04W 88/02*   (2009.01)
(52) U.S. Cl.
USPC ......... 455/100; 455/41.1; 455/41.2; 455/101; 455/552.1; 340/539.12
(58) Field of Classification Search
USPC ............ 455/100, 41.1, 41.2, 101, 552.1, 103; 340/539.12, 539.22, 539.26, 539.13, 340/539.14; 600/300–301
See application file for complete search history.

(56) References Cited

U.S. PATENT DOCUMENTS

| 8,095,177 | B2 * | 1/2012 | Ida .............................. 455/552.1 |
| 8,199,000 | B2 * | 6/2012 | Ross et al. ............... 340/539.12 |
| 8,535,223 | B2 * | 9/2013 | Corroy et al. ................. 600/300 |
| 2004/0138723 | A1 | 7/2004 | Malick |
| 2007/0286274 | A1 | 12/2007 | Julian |
| 2008/0262376 | A1 | 10/2008 | Price |
| 2009/0023391 | A1 * | 1/2009 | Falck ........................... 455/41.2 |

FOREIGN PATENT DOCUMENTS

| EP | 1220501 A2 | 3/2002 |
| WO | WO2007084807 A1 | 7/2007 |
| WO | WO2007096810 A1 | 8/2007 |

OTHER PUBLICATIONS

Thomas G. Zimmerman, "personal Area networks (PAN): Near-Field Intra-Body Communication", Master of Science in Media Arts and Sciences, Massachusetts Institute of Technology, Sep. 1995.
Lin Zhong et al., "OsteoConduct: Wireless Body-Area Communication Based on Bone Conduction", Dept. of Electrical and Computer Engineering, Dept. of Bioengineering, Rice University.
IEEE P802.15 Wireless Personal Area Networks, "IEEE P802.15 TG6 (Body Area Network) Call for Applications", Jan. 2008.
A. Fazzi et al., "ADA—Physical Link: Report on Transmission Analysis", Technical Note PR-TN 2007/00428, Issued: Jul. 2007.

* cited by examiner

*Primary Examiner* — Pablo Tran
(74) *Attorney, Agent, or Firm* — Larry Liberchuk

(57) ABSTRACT

In summary, the present invention relates to a device, a method, a system and a computer program enabling to ensure a reliable communication even under difficult radio frequency conditions. In case data cannot be successfully communicated by a radio frequency communication, the data may be transmitted to another device by a body-coupled communication via a human or animal body. The other device can act as a relay and forward the data to an intended destination. Thus, data may be successfully transmitted to the intended destination even under difficult radio frequency conditions due to body shadowing or other effects.

12 Claims, 9 Drawing Sheets

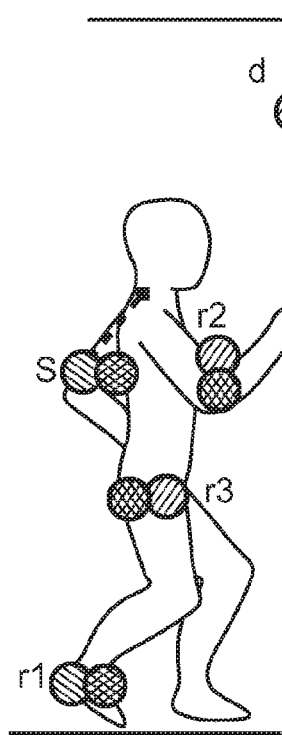 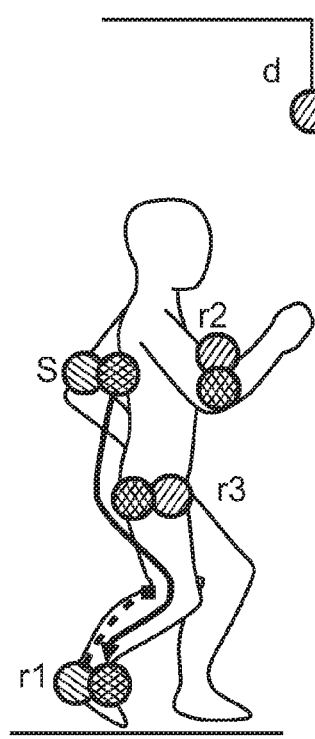 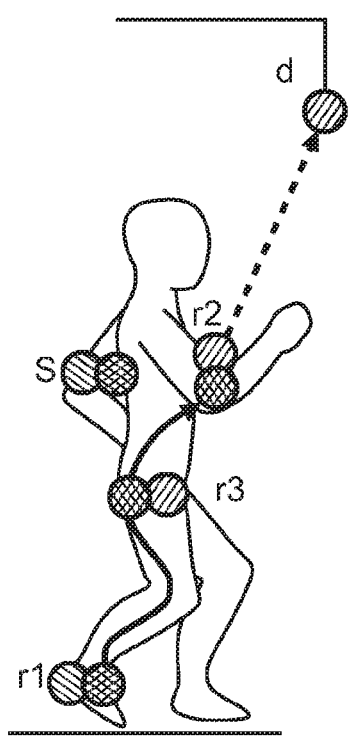
Fig. 7    Fig. 8    Fig. 9
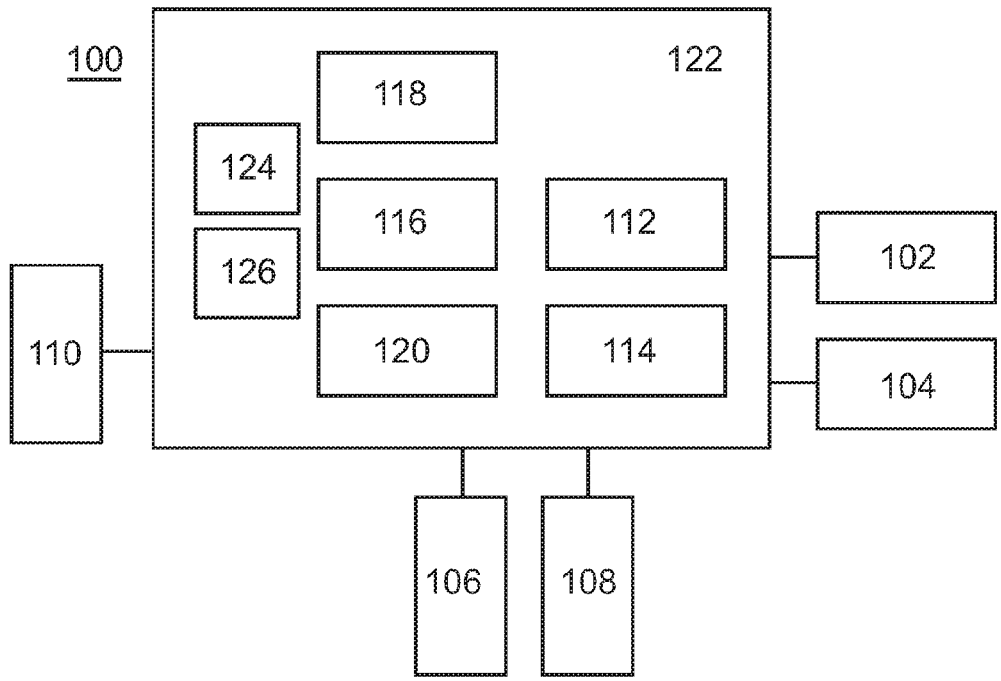
Fig. 10

COMBINING BODY-COUPLED COMMUNICATION AND RADIO FREQUENCY COMMUNICATION

FIELD OF THE INVENTION

The present invention generally relates to a device, a system, a method and a computer program for providing a reliable on-body and off-body wireless connectivity by combining a body-coupled communication and a radio frequency communication.

BACKGROUND OF THE INVENTION

Body-coupled communication (BCC) allows exchange of information between devices that are located at or in close proximity of a human or animal body. BCC signals are conveyed over the body instead of through the air. The body (and the space few centimeters around it) is utilized as a communication channel, thus allowing for touch-based interaction and data exchange. A detailed description of the basic underlying communication principle is given by Thomas Guthrie Zimmerman, "Personal Area Networks (PAN): Near-Field Intra-Body Communication", MASTER OF SCIENCE IN MEDIA ARTS AND SCIENCES at the Massachusetts Institute of Technology, September 1995. In this thesis, the term "near-field intra-body communication" is used when describing a body-coupled or body-based communication.

A communication based on BCC signals is confined to an area close to the body. This is in contrast to radio frequency (RF) communications, where a much larger area is covered. Thus, when using BCC signals, a communication is only possible between devices situated on, connected to or placed close to the same body.

On the other hand, RF communication technologies using a high frequency like e.g. low power short range RF technologies operating in the 2.4 GHz industrial, scientific and medical (ISM) band such as IEEE 802.15.4 ("ZigBee") technologies are well suited for off-body communication under line-of-sight conditions. However, they are not well suited to operate around the human body. They suffer from high body shadowing or attenuation leading to unreliable communication. This frequently happens in scenarios where two body sensors want to talk with each other or the human or animal body blocks the direct line-of-sight between an on-body sensor and an off-body device. For example, a node on the chest of a user cannot communicate to another node on the back of the user. As RF systems use crowded free frequency bands, they suffer from interference. This again decreases the reliability of the communication. Further, RF systems exhibit a very high power consumption leading to short system lifetime and expensive and cumbersome battery management.

Providing a reliable wireless connectivity is advantageous for healthcare applications and other applications relying on networked on-body sensors and/or actuators as well as off-body devices. One example of such applications is automatic fall detection (AFD) in houses of elderly persons by means of a body area network (BAN). Each elderly person wears sensors such as e.g. accelerometers to detect if the person falls. In that case an alarm is sent via a wireless infrastructure based on e.g. WiFi or Zigbee technology. In some scenarios, e.g. if the elderly person falls on one or more sensors, at least part of the sensors cannot communicate anymore with the wireless infrastructure. As a result, it can be impeded that any alarm is sent.

FIGS. 18 to 21 illustrate the body shadowing of a RF communication in an AFD application. FIG. 18 illustrates a normal case of RF communication. Back and front nodes BN, FN such as sensors attached to the back and front of an elderly person can communicate with an off-body destination d such as e.g. an access point (AP) in the form of a device mounted e.g. to a room ceiling. FIG. 19 illustrates a front case of RF communication. Only the front node FN is able to communicate with the destination d. FIG. 20 illustrates a back case of RF communication. Only the back node BN can communicate with the destination d. FIG. 21 illustrates a fall case of RF communication. Only the back node BN is able to communicate with the destination d.

Another example is patient monitoring in hospitals by using body-worn medical sensors such as e.g. electrocardiogram (ECG), pulse oximetry (SpO2) and blood pressure sensors. These sensors may wirelessly transmit their measurements via a short range radio to a nearby patient monitor (if the patient is lying in his bed) ["off-body communication"] or to a body-worn hub ["on-body communication"] that forwards the data via an infrastructure based on wireless local area network (WLAN) technology to a central nurse station (if the patient walks around the hospital). A medical-grade wireless connectivity is required for patient monitoring in hospitals.

FIGS. 22 and 23 illustrate an example of patient monitoring in hospitals. FIG. 22 illustrates an example of patient monitoring at the bedside. In this case, first and second sensors 1, 2 can directly communicate with a bedside monitor 3 that is connected to a patient information centre 4 via a network 5. A hub 0 is not used. FIG. 23 shows an example of patient monitoring while a patient is ambulating. In this case, the first and second sensors 1, 2 may communicate with a hub 0, which in turn can communicate with an AP 7 such as e.g. an off-body device mounted e.g. to a room ceiling and connected to the patient information centre 4 via the network 5.

A wireless link quality to an off-body device varies depending on the position of a short range radio on the body of the patient for transmitting sensor measurements. Further, the RF conditions change dynamically due to the movement of the patient.

FIGS. 24 and 25 illustrate the dynamically changing wireless link quality. FIG. 24 illustrates a scenario where the second sensor 2 has a better wireless link quality. The sensor 2 has a better wireless link quality to the bedside monitor 3 than the sensor 1, i.e. a link quality indication (LQI) of the sensor 2 is higher than a LQI of the sensor 1. That is, in the scenario of FIG. 24 LQI(1→3)<LQI(2→3) applies. FIG. 25 illustrates a scenario where the first sensor 1 has a better wireless link quality. The RF conditions are reversed, i.e. the sensor 1 has a better wireless link quality to the bedside monitor 3 (higher LQI) than the sensor 2. That is, in the scenario of FIG. 25 LQI(1→3)>LQI(2→3) applies.

On the other hand, BCC technologies based on e.g. capacitive coupling or bone conduction are well suited for on-body communication, but are unable to provide connectivity to off-body devices.

As a result, neither RF nor BCC alone can meet the connectivity requirements of body-worn sensors as demanded for healthcare applications such as e.g. patient monitoring in hospitals and other applications such as e.g. AFD. This fact has also been recognized by the IEEE 802.15.6 BAN working group, which aims for specifying three different wireless technologies for on-body, off-body and in-body communication, respectively.

SUMMARY OF THE INVENTION

It is an object of the present invention to alleviate at least some of the above described problems.

This object can be achieved by a device according to claim 1, a system according to claim 24, a method according to claim 25, and a computer program according to claim 26.

Accordingly, in a first aspect of the present invention a device is presented. The device can comprise a body-coupled communication unit configured to perform a body-coupled communication via a human or animal body, a radio frequency communication unit configured to perform a radio frequency communication, and a processing unit configured to decide whether data shall be transmitted by the body-coupled communication unit or the radio frequency communication unit to a destination or transmitted by the body-coupled communication unit to an intermediate device configured to try to transmit the data by a radio frequency communication to the destination. The device can forward data to an intermediate device by its body-coupled communication unit, if it is not able to transmit the data by its radio frequency communication unit or the intermediate device provides a better radio frequency link quality. The intermediate device may then transmit the data by its radio frequency communication unit. In this way, a reliable communication with an off-body destination can be enabled even if some devices of a network cannot perform a successful radio frequency communication due to e.g. body shadowing or attenuation. The device enables to provide medical-grade wireless connectivity to body-worn sensors and other units for both on-body and off-body communication. It addresses the body attenuation problem of low power RF communication.

In a second aspect of the present invention the processing unit may be configured to decide to which intermediate device the data shall be transmitted by the body-coupled communication unit. Thus, an intermediate device suitable to transmit the data by a radio frequency communication can be selected. The second aspect may be combined with the first aspect.

In a third aspect of the present invention the device can comprise a determining unit configured to determine whether the data has been successfully transmitted to the destination, wherein the processing unit may be configured to decide to which intermediate device the data shall be transmitted by the body-coupled communication unit, if a determination by the determining unit is negative. Hence, an intermediate device suitable to transmit the data by a radio frequency communication can be selected in case a transmission of the data by the radio frequency communication unit has failed. The third aspect may be combined with any one of the preceding aspects.

In a fourth aspect of the present invention the device can comprise a storing unit configured to store a first list of other devices in a body-coupled communication network comprising the device. As the available devices can be gathered from the first list, an alternative device may be quickly found. The fourth aspect can be combined with any one of the preceding aspects.

In a fifth aspect of the present invention based on the fourth aspect the processing unit may be configured to decide to transmit the data by the body-coupled communication unit to the destination, if the destination is present in the first list. Thus, based on the contents of the first list it can be easily decided to use the body-coupled communication unit for transmitting the data to the destination.

In a sixth aspect of the present invention based on the fourth aspect the processing unit may be configured to decide to first try to transmit the data to the destination by the radio frequency communication unit, if the destination is not present in the first list. As the device tries first to transmit data by its own radio frequency communication unit, there is little delay in transmitting data packets to an off-body destination in case there are good radio frequency conditions such as e.g. line-of-sight conditions. Thus, there is a very low latency. Moreover, if the device is moving, the fact that it first tries to communicate via radio frequency and then tries to find an alternative device enables to quickly react to new radio frequency neighbours, i.e. to be very dynamic. The sixth aspect can be combined with the fifth aspect.

In a seventh aspect of the present invention the body-coupled communication unit may be configured to transmit to the intermediate device an address of a source of the data, an address of the destination and a list of addresses of devices, including an address of the device, that already failed to successfully transmit the data by their respective radio frequency communication unit. The transmitted information enables the intermediate device to know which devices have not yet failed to successfully transmit the data. Thus, it can forward the data to one of these devices in case it also fails to successfully transmit the data. The seventh aspect may be combined with any one of the preceding aspects.

In an eighth aspect of the present invention based on the fourth aspect the processing unit can be configured to randomly select the intermediate device from the first list, excluding a source of the data and devices that already failed to successfully transmit the data by their respective radio frequency communication unit. As the available devices may be gathered from the first list, an alternative device may be quickly found. The eighth aspect can be combined with the fifth or sixth aspect.

In a ninth aspect of the present invention based on the third aspect the body-coupled communication unit may be configured to receive from another device an address of a source of the data, an address of the destination and a list of addresses of devices that already failed to successfully transmit the data by their respective radio frequency communication unit, and the processing unit can be configured to decide to transmit by the body-coupled communication unit to the source of the data an indication that the data has been successfully transmitted, if the determination by the determining unit is positive, transmit by the body-coupled communication unit to the source of the data an indication that the data has not been successfully transmitted, if the determination by the determining unit is negative and there are no other devices than the device, the source of the data and the devices the addresses of which are contained in the list of addresses of devices, and transmit by the body-coupled communication unit to the intermediate device the address of the source of the data, the address of the destination and the list of addresses of devices, supplemented by an address of the device, that already failed to successfully transmit the data by their respective radio frequency communication unit, if the determination by the determining unit is negative and an address of the intermediate device is neither identical to the address of the source of the data nor contained in the list of addresses of devices. This enables to inform a source of data about the result of trying to transmit the data by alternative devices. Moreover, an intermediate device can be informed about the source of the data and the devices that already failed to successfully communicate the data, so that it can inform the source of the data about a communication result or forward the data to a further intermediate device.

In a tenth aspect of the present invention the body-coupled communication unit may be configured to receive from another device an indication that the data has been successfully transmitted or not. This enables to provide a feedback on the communication result. The tenth aspect can be combined with any one of the preceding aspects.

In an eleventh aspect of the present invention based on the fourth aspect the storing unit may be configured to store for each possible destination, that is not present in the first list, a respective most successful device, that is present in the first list, and number of successful radio frequency communications of the most successful device. Storing the most successful device and number of successful radio frequency communications enables to learn which is a best relay for a specific destination. The eleventh aspect can be combined with any one of the fifth, sixth and eighth aspects.

In a twelfth aspect of the present invention based on the eleventh aspect the processing unit may be configured to decide to transmit the data to a most successful device stored in the storing unit for the destination. This enables to purposefully forward the data.

In a thirteenth aspect of the present invention based on the eleventh aspect the device can comprise a determining unit configured to determine whether a successful radio frequency communication with the destination has been performed by the radio frequency communication unit, and a modifying unit configured to modify contents of the storing unit, wherein the body-coupled communication unit may be configured to receive an indication that a successful radio frequency communication with the destination has been performed by a radio frequency communication unit of the intermediate device, and wherein the modifying unit can be configured to store in the storing unit the device as a most successful device for the destination together with a number of one, if the determination by the determining unit is positive and no most successful device for the destination exists, increase in the storing unit the number for the destination and the device, if the determination by the determining unit is positive and the device is already stored as a most successful device for the destination, store in the storing unit the intermediate device as a most successful device for the destination together with a number of one, if the body-coupled communication unit receives the indication and no most successful device for the destination exists, and increase in the storing unit the number for the destination and the intermediate device, if the body-coupled communication unit receives the indication and the intermediate device is already stored as a most successful device for the destination. This enables to keep the contents of the storing unit up-to-date, so that a most promising device may be gathered from the storing unit. The thirteenth aspect can be combined with the twelfth aspect.

In a fourteenth aspect of the present invention based on the eleventh aspect the device may comprise a comparing unit configured to compare a threshold value and a respective number associated with the destination and a respective device, wherein the processing unit can be configured to decide to transmit the data to a most successful device by the body-coupled communication unit, if a number associated with the destination and the most successful device is greater than the threshold value, and wherein the processing unit may be configured to decide to try to transmit the data by the radio frequency communication unit, if none of the numbers is greater than the threshold value. In this way, data intended for a specific destination can always be forwarded to some other device, if that other device has proved to be suitable for that specific destination for a certain number of times. Otherwise, an alternative device can be randomly chosen. The fourteenth aspect can be combined with the twelfth or thirteenth aspect.

In a fifteenth aspect of the present invention the device may comprise a determining unit configured to determine whether the data has been successfully transmitted to the destination by the intermediate device, wherein the processing unit can be configured to decide to which further intermediate device the data shall be transmitted by the body-coupled communication unit, if a determination by the determining unit is negative. Thus, if a transmission of the data by the intermediate device has failed, then a further intermediate device suitable to transmit the data by a radio frequency communication may be selected. The fifteenth aspect can be combined with any one of the preceding aspects.

In a sixteenth aspect of the present invention based on the fourth aspect the storing unit may be configured to store a second list indicating for each possible destination which device provides a best radio frequency link quality. The second list enables to easily select a device providing a best radio frequency link quality for a specific destination, i.e. being most suitable for a radio frequency communication with that destination. The sixteenth aspect can be combined with any one of the fifth, sixth, eighth, eleventh, twelfth, thirteenth and fourteenth aspects.

In a seventeenth aspect of the present invention based on the sixteenth aspect the processing unit may be configured to determine based on the second list whether the device or another device from the first list provides a best radio frequency link quality for the destination, wherein the processing unit can be configured to decide to transmit the data by the radio frequency communication unit, if the processing unit determines that the device provides a best radio frequency link quality for the destination, and wherein the processing unit may be configured to decide to transmit the data by the body-coupled communication unit to the intermediate device, if the processing unit determines that the intermediate device provides a best radio frequency link quality for the destination. In this way, the data can be transmitted by a device providing a best radio frequency link quality for a specific destination, i.e. being most suitable for a radio frequency communication with that destination.

In an eighteenth aspect of the present invention based on the fourth aspect the body-coupled communication unit may be configured to transmit to other devices from the first list at least one radio frequency link quality indication associated with the device and a respective destination. Other devices can be informed on the radio frequency link quality of a current device for a certain destination. In this way, each of the devices may know which device is currently the most suitable one for the certain destination. The eighteenth aspect can be combined with any one of the fifth, sixth, eighth, eleventh, twelfth, thirteenth, fourteenth, sixteenth and seventeenth aspects.

In a nineteenth aspect of the present invention based on the sixteenth aspect the processing unit may be configured to check whether it is indicated in the second list which device provides a best radio frequency link quality for the destination, wherein the processing unit can be configured to instruct each device from the first list to report its respective radio frequency link quality indication associated with the destination, if a result of a check by the processing unit is negative, and wherein the body-coupled communication unit may be configured to respectively transmit an instruction from the processing unit to a device from the first list. If no information regarding a most suitable device for a certain destination is available, the device may request the present radio frequency link qualities from other devices. In this way, it can proactively obtain new information. The nineteenth aspect may be combined with the seventeenth aspect.

In a twentieth aspect of the present invention the body-coupled communication unit can be configured to receive an instruction to report a radio frequency link quality indication associated with the device and a respective destination, the radio frequency communication unit may be configured to transmit a message to the respective destination and to receive a response to the message from the respective destination, and the processing unit can be configured to report by the body-coupled communication unit a radio frequency link quality indication resulting from the response to the message, if the radio frequency link quality indication exceeds a specified threshold. The device may perform a new determination of the radio frequency link quality on request. Thus, it can supply a radio frequency link quality indication that is up-to-date. The twentieth aspect may be combined with any one of the preceding aspects.

In a twenty-first aspect of the present invention based on the fourth aspect the body-coupled communication unit can be configured to receive a message indicating an address of another device from the first list and whether the other device is a radio frequency hub device, wherein the processing unit may be configured to update an entry for the other device in the first list with contents of the message and a time stamp of a current time, if the message is received by the body-coupled communication unit, and to remove entries with time stamps older than a first maximum expiration time from the first list. The device can know which one of other devices is a hub to be used for forwarding data if all devices are out of range to a destination. It may be prevented that such information and other information about a device is out of date, by deleting it in case its time stamp is too old. The twenty-first aspect can be combined with any one of the fifth, sixth, eighth, eleventh, twelfth, thirteenth, fourteenth, sixteenth, seventeenth, eighteenth and nineteenth aspects.

In a twenty-second aspect of the present invention based on the sixteenth aspect the body-coupled communication unit may be configured to receive a radio frequency link quality indication associated with another device from the first list and a respective destination, and the processing unit can be configured to store, if no entry for the respective destination exists, in the second list for the respective destination the radio frequency link quality indication received by the body-coupled communication unit, an address of the other device and a time stamp of a current time, update an entry for the respective destination in the second list with a time stamp of a current time and, if the radio frequency link quality indication received by the body-coupled communication unit is greater than an already stored radio frequency link quality indication for the respective destination, with the received radio frequency link quality indication and the address of the other device, and remove entries with time stamps older than a second maximum expiration time from the second list. In this way, it may be ensured that a device has up-to-date information regarding a most suitable device for a certain destination. Thus, data for the destination can be directly forwarded to the appropriate device. The twenty-second aspect may be combined with the seventeenth or nineteenth aspect.

In a twenty-third aspect of the present invention based on the fourth aspect the processing unit can be configured to inspect the first list in order to check whether there is a radio frequency hub device in the body-coupled communication network, if the intended destination is out of range for all devices from the first list, wherein the processing unit may be configured to decide to transmit the data by the body-coupled communication unit to the radio frequency hub device, if a result of a check by the processing unit is positive. If the device determines that a radio frequency hub device is available, it can forward data to the radio frequency hub device in case the distance to the intended destination is too great. Thus, a reliable communication with an off-body destination may be ensured even for a greater distance. The twenty-third aspect can be combined with any one of the fifth, sixth, eighth, eleventh, twelfth, thirteenth, fourteenth, sixteenth, seventeenth, eighteenth, nineteenth, twenty-first and twenty-second aspects.

In a twenty-fourth aspect of the present invention a system is presented. The system may comprise a plurality of devices according to any one of the preceding aspects, and a radio frequency hub device configured to relay the data if the destination is out of range for all of the plurality of devices. If a device has no good radio frequency conditions, it can forward data either to another device having better radio frequency conditions or to the radio frequency hub device enabling a communication over a greater distance. Thus, a reliable communication with an off-body destination may be ensured.

In a twenty-fifth aspect of the present invention a method is presented. The method can comprise deciding whether data shall be transmitted by a body-coupled communication unit or a radio frequency communication unit of a device to a destination, and deciding whether the data shall be transmitted by the body-coupled communication unit to an intermediate device configured to try to transmit the data by a radio frequency communication to the destination. Data may be forwarded to an intermediate device by the body-coupled communication unit, if it could not be successfully communicated by the radio frequency communication unit or the intermediate device provides a better radio frequency link quality. The intermediate device can then transmit the data by a radio frequency communication. In this way, a reliable communication with an off-body destination may be enabled even if some devices of a network cannot perform a successful radio frequency communication due to e.g. body shadowing or attenuation. A medical-grade wireless connectivity to body-worn sensors and other units for both on-body and off-body communication can be achieved.

In a twenty-sixth aspect of the present invention a computer program is presented. The computer program may comprise program code means for causing a computer to carry out the steps of a method according to the twenty-fifth aspect when the computer program is carried out on a computer. Thus, the same advantages as with the method according to the twenty-fifth aspect can be achieved.

Further advantageous modifications are defined in the dependent claims.

BRIEF DESCRIPTION OF THE DRAWINGS

These and other aspects of the present invention will be apparent from and elucidated by embodiments described hereinafter with reference to the accompanying drawings, in which:

FIG. 7 illustrates a scenario where a device according to the first embodiment cannot successfully communicate with an off-body destination;

FIG. 8 illustrates a scenario where a device according to the first embodiment tries to forward data to an off-body destination, but cannot successfully communicate with the same;

FIG. 9 illustrates a scenario where a device according to the first embodiment forwards data to an off-body destination;

FIG. 10 shows a schematic block diagram illustrating an exemplary arrangement of a device according to a second embodiment;

DETAILED DESCRIPTION OF EMBODIMENTS

Figure 1:
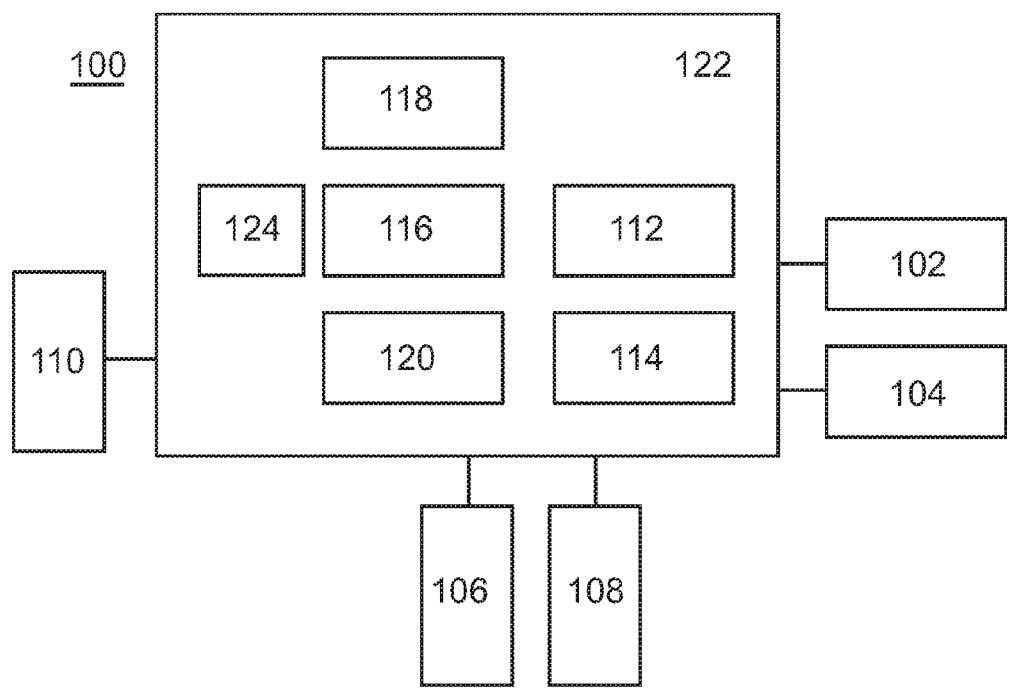
FIG. 1 shows a schematic block diagram illustrating an exemplary arrangement of a device according to a first embodiment.

FIG. 1 shows a schematic block diagram illustrating an exemplary arrangement of a device 100 according to a first embodiment. The device 100 may be some kind of sensor platform or sensor device, even if no sensors have to be attached to it. It can comprise a body-coupled communication (BCC) unit 102, a radio frequency (RF) communication unit 104, a first sensor unit 106, a second sensor unit 108, a power supply 110, a processor or processing unit 112, a determining unit 114, a memory or storing unit 116, a modifying unit 118, and a comparing unit 120. The processing unit 112, the determining unit 114, the storing unit 116, the modifying unit 118 and the comparing unit 120 may be part of a microcontroller 122 or other component. Further, the microcontroller 122 can have the functionality of one or more of these units, so that they may not exist as separate components. If it has this functionality, it can process an application as well as a communication protocol stack. Moreover, two or more of the units may be integrated in a single component other than the microcontroller 122, even if this is not depicted in FIG. 1. Furthermore, there can be an alternative number of sensor units. For example, no sensor unit at all or more than two sensor units may be present.

The BCC unit 102 such as e.g. a BCC transceiver can perform a body-coupled communication via a human or animal body. The RF communication unit 104 such as e.g. a RF transceiver may conform e.g. to IEEE 802.15.4 or some other standard and perform a radio frequency communication with a destination such as e.g. an off-body destination. The first and second sensor units 106, 108 can respectively perform a physiological measurement at the human or animal body or another measurement. For example, electrocardiogram (ECG), pulse oximetry (SpO2), blood pressure measurements, etc. are possible. Further, an accelerometer may be used as a sensor unit, to determine e.g. in case of an automatic fall detection (AFD) application that a person falls. Data transmitted by the BCC unit 102 and/or the RF communication unit 104 may comprise measurement data provided by one or more of the sensor units 106, 108. The power supply 110 can supply power for the whole device 100.

The processing unit 112 may decide whether data shall be transmitted by the BCC unit 102 or the RF communication unit 104 to a destination or transmitted by the BCC unit 102 to an intermediate device, which is described in more detail below. The intermediate device can be e.g. another device 100 and may try to transmit the data by a RF communication to the destination. The processing unit 112 may also decide to which intermediate device the data shall be transmitted by the BCC unit 102, i.e. select an intermediate device. This decision can be made in dependence on a determination by the determining unit 114 as described in more detail below. Moreover, the processing unit 112 may make other decisions and have additional functionalities as described below.

The determining unit 114 can determine whether data has been successfully transmitted to the destination. For example, it may determine whether the data has been successfully transmitted by the BCC unit 102 or the RF communication unit 104. The processing unit 112 can decide to which intermediate device the data shall be transmitted by the BCC unit 102, if a determination by the determining unit 114 is negative. That is, it may select a further device to which data is to be transmitted by means of the BCC unit 102, if the data could not be successfully transmitted by the RF communication unit 104.

The storing unit 116 can store various information as described in more detail below. In particular, it may store a first list 124 of devices in a BCC network including the device 100. The modifying unit 118 can modify contents of the storing unit 116 as described in more detail below. The comparing unit 120 may compare a threshold value and a number of successful RF communications as described in more detail below.

Figure 2:
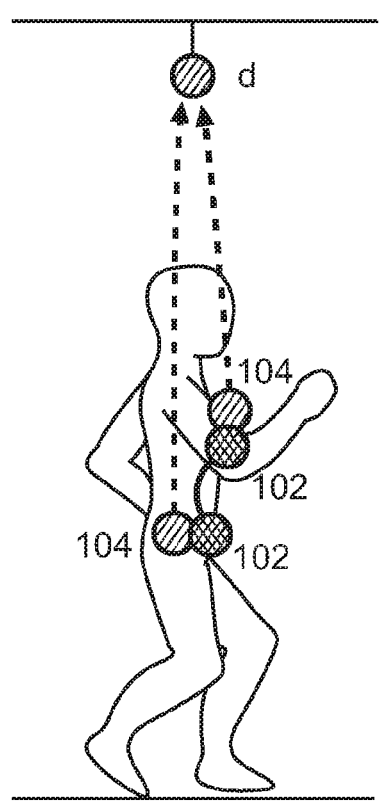
FIG. 2 shows a basic system comprising devices according to the first embodiment.

FIG. 2 shows a basic system comprising devices 100 according to the first embodiment. In FIG. 2 and the following figures only respective BCC and RF communication units 102, 104 of each device 100 are represented. In the depicted example, the system is a body area network (BAN) comprising two devices 100 attached to a human body. In general, the system can comprise any number of devices 100. As shown in FIG. 2, the BCC units 102 of the different devices 100 may communicate with each other. Further, each of the RF communication units 104 can communicate with an off-body destination d such as e.g. a RF transceiver mounted e.g. to a room ceiling, provided that sufficient RF conditions are available.

In the following, the devices 100 may be called "nodes", a node where data originate from can be called "source", a node forwarding data and acting as a relay, i.e. an intermediate device 100, may be called "relay", and the off-body destination can be referred to as "destination" only. All nodes on the body may comprise both a BCC unit 102 and a RF communication unit 104.

Figure 3:
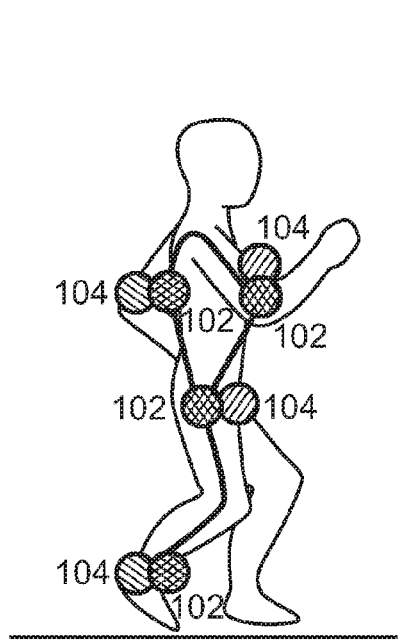
FIG. 3 illustrates a scenario where an on-body communication between devices according to the first embodiment takes place.

FIG. 3 illustrates a scenario where an on-body communication between devices 100 according to the first embodiment takes place. The devices 100 may communicate with each other by means of their respective BCC units 102. That is, when a device 100 on the body wants to communicate with another device 100 on the body, it can use its BCC unit 102. As all the communication on the body may be processed with BCC, a considerable amount of energy can be saved in comparison with an on-body communication by using RF technologies.

Figure 4:
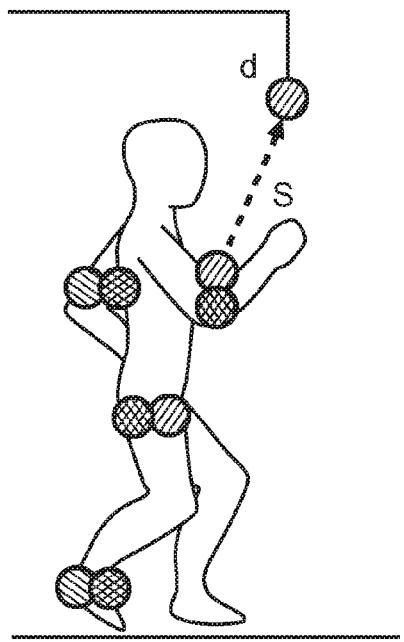
FIG. 4 illustrates a scenario where a device according to the first embodiment directly communicates with an off-body destination.

FIG. 4 illustrates a scenario where a device 100 according to the first embodiment directly communicates with an off-body destination d. When the source s on the body wants to communicate with the destination d outside the body, it can first try to transmit with its own RF communication unit 104. This decision to first try to transmit the data to the destination d by the RF communication unit 104 may be made by the processing unit 112 if the destination d such as e.g. a RF transceiver is not present in the first list 124. In the example shown in FIG. 4, the source s is able to directly communicate with the destination d, as it has a line-of-sight to the destination d, i.e. there are good RF conditions.

Figure 5:
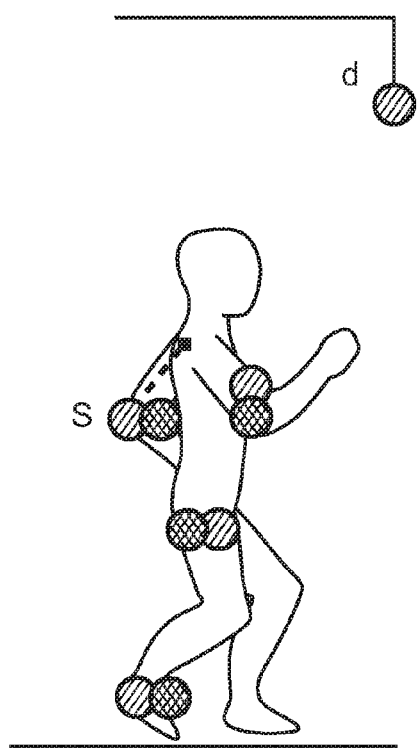
FIG. 5 illustrates a scenario where a device according to the first embodiment cannot directly communicate with an off-body destination.

FIG. 5 illustrates a scenario where a device 100 according to the first embodiment cannot directly communicate with an off-body destination d. If the source s has no line-of-sight to the destination d as in the example shown in FIG. 5, the body may absorb the entire RF signal transmitted by the RF communication unit 104 of the source s (this effect is known as shadowing) as illustrated in FIG. 5. As a result, no successful RF communication between the source s and the destination d is possible. Thus, the determining unit 114 can determine that data has not been successfully transmitted to the destination d. That is, a determination by the determining unit 114 may be negative.

Figure 6:
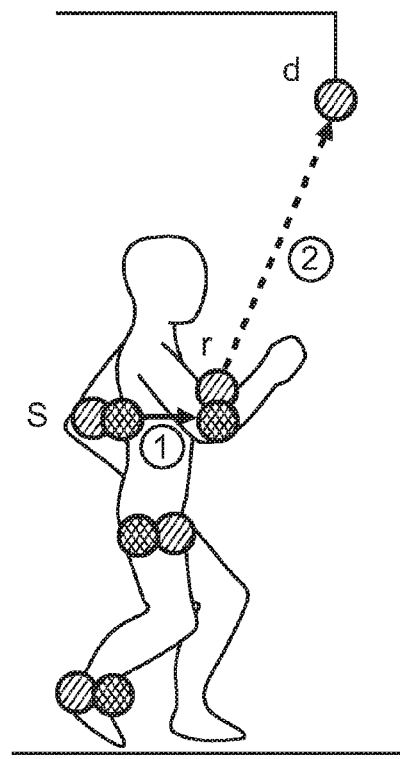
FIG. 6 illustrates a scenario where a device according to the first embodiment communicates with an off-body destination via a further device.

FIG. 6 illustrates a scenario where a device 100 according to the first embodiment communicates with an off-body destination d via a further device 100, i.e. an intermediate device. When the source s starts a transmission of data, it can trigger a timer. The timer may be implemented e.g. in the determining unit 114 of the source s. When the timer is elapsed and the source s did not receive any data back from the destination d, then it can assume that the communication failed. That is, the determining unit 114 may determine that the data has not been successfully transmitted. Then, the source s can apply the following methodology:

(1) The source s may transmit the data to another node on the body with BCC. That is, the BCC unit 102 of the source s can transmit the data to the BCC unit 102 of a relay r. The procedure of choosing the relay is described in more detail below.

(2) The relay r may forward the received data to the destination d by using its own RF communication unit 104.

If the relay r also fails to reach the destination d, then it can forward the data to another node on the body, which may also try to reach the destination d. This procedure can be repeated until the communication is successful or until all the nodes on the body failed. Next, it is described in more detail how the source s searches for a relay.

A BCC network is a single-hop network, so that all nodes on the body can reach all other nodes on the body. Each node may maintain a list of all other nodes present in the network. That is, a respective first list 124 of all other devices in a BCC network can be stored in the respective storing unit 116 of each device 100.

When a node enters the BCC network, it may broadcast its address so that other nodes can insert it in their respective first list 124. When a node leaves the network, it may also broadcast its address so that other nodes can remove it from their respective first list 124. Each node may keep its first list 124 up-to-date by observing the traffic or eventually periodically broadcast its presence or transmit to a specific node a presence request (i.e. ask a node if it is still alive). This maintenance can be exclusively done with BCC.

If the source s must use a relay r for reaching a destination d outside the body, then it may randomly pick one node from its first list 124 of other nodes in the BCC network, which list can be considered a neighbour list. That is, the processing unit 112 of a device 100 acting as the source s may randomly select an intermediate device 100 from the first list 124. Next, the source s can transmit the data intended for the destination d to the selected relay r, wherein a data packet may contain:
  The data
  The address of the source s
  The address of the destination d
  A list of addresses of the relays that already got the packet and failed to perform a successful RF communication Thus, when a relay r gets a packet to forward, if the list of failed relays is empty then the relay r is the first to get the data from the source s. If a relay r fails, then it can randomly pick a node in the neighbour list excluding the source s and all the already failed relays. That is, the processing unit 112 of the device 100 acting as the relay r may select an intermediate device 100 excluding the source s and all devices 100 that already failed to transmit the data by their respective RF communication unit 104. Then, it can add the address of the device 100 presently acting as a relay to the list of failed relays and forward the data to the randomly picked new relay. FIGS. 7 to 9 illustrate an example of this procedure for a system comprising four nodes, i.e. a source s and three relays r1, r2, r3.

FIG. 7 illustrates a scenario where a device 100 according to the first embodiment cannot successfully communicate with an off-body destination d. The device 100 acting as a source s wants to send a data packet to the destination d. The source s has no line-of-sight to the destination d. Therefore, the source s cannot perform a successful RF communication with the destination d, i.e. the RF communication fails. The first list 124 of all other devices in the BCC network as stored in the storing unit 116 of the source s is {r1, r2, r3}. The list of failed relays in a data packet from the source s to the destination d is {0}, i.e. is empty.

FIG. 8 illustrates a scenario where a device 100 according to the first embodiment tries to forward data to an off-body destination d, but cannot successfully communicate with the same. The device 100 acting as a source s can randomly pick or select an intermediate device 100 as a relay r1, by means of its processing unit 112. Then, it may forward the data packet to the relay r1, by means of its BCC unit 102. Next, the relay r1 can try to transmit the data by its RF communication unit 104. As the relay r1 also has no line-of-sight to the destination d, it cannot perform a successful RF communication with the destination d. That is, it fails to reach the destination d with RF. The first list 124 of all other devices in the BCC network as stored in the storing unit 116 of the source s is {r1, r2, r3}. The list of failed relays in a data packet from the source s to the relay r1 is {0}, i.e. is empty.

FIG. 9 illustrates a scenario where a device 100 according to the first embodiment forwards data to an off-body destination d. The device 100 acting as a relay r1 can randomly select a further intermediate device 100 as a relay r2, by means of its processing unit 112. Then, it may forward the data packet to the relay r2, by means of its BCC unit 102. Next, the relay r2 can try to transmit the data by its RF communication unit 104. As the relay r2 has line-of-sight to the destination d, it can perform a successful RF communication with the destination d, i.e. successfully reach the destination d with RF. The first list 124 of all other devices in the BCC network as stored in the storing unit 116 of the relay r1 is {r2, r3, s}. The list of failed relays in a data packet from the relay r1 to the relay r2 is {r1}, i.e. comprises the relay r1 that previously failed.

At the end of the above procedure, the source s may get a feedback packet back. This may happen in the following cases:
(1) If a relay is successful, i.e. a determination by its determining unit 114 is positive, it does not continue to forward the data to other relays and sends a packet to the source indicating that the communication was successful.
(2) If a relay fails to reach the destination d, i.e. a determination by its determining unit 114 is negative, and its list of failed relays contains all other nodes in the BCC network (of course excluding itself and the source s), then all nodes failed. Thus, it sends a packet to the source s indicating that the communication failed. Hence, an indication that data has not been successfully transmitted can be transmitted to the source s.

All nodes in the network can "learn" which is the best relay to join a specific destination. Each node can maintain a table of possible destinations and current best relay for the respective destination. The table may be stored e.g. in the storing unit 116 of the node or in another storing unit of the node. When a node starts a communication with a specific destination and uses a relay to make it successful, it can get a feedback from a node that was actually successful. Then, it may associate this successful node to the specific destination as well as a counter in the table. If a best relay for a destination does not already exist, the first relay enabling a successful communication to the destination can be associated to this destination with a counter equal to one. Each time this relay enables another successful communication to this destination, the counter may be increased by one. If the best relay fails and another relay enables a successful communication to the destination, then this new relay can be associated to the destination with a counter equal to one. Thus, for each possible destination a respective most successful node and number of successful radio frequency communications of the most successful node may be stored.

That is, the determining unit 114 of a node can determine whether a successful RF communication with a destination has been performed by the RF communication unit 104 of the node. The BCC unit 102 of the node may receive an indication that a successful RF communication with the destination has been performed by the RF communication unit 104 of another node. The modifying unit 118 of the node can modify the contents of the storing unit 116 of the node accordingly.

A threshold value C may be decided, wherein C can be equal to or greater than one. Each time a node wants to transmit a packet to another node outside the body, i.e. a destination d, the following procedure may be carried out:

If the counter associated with a best relay for the destination is smaller than C, then the node can follow the previously described procedure (i.e. send itself first and then randomly pick the relays).
If the counter associated with a best relay for the destination is greater than C, then the node may forward the packet directly to the best relay.
If the best relay fails, then it can follow the random procedure detailed above.

The value of C can be chosen by a programmer. A small value of C is good for a fixed scenario where the body to which the nodes are attached does not move. In this case, the best relays may be found quickly and stay valid for a long time.

On the other side, if the user moves a lot, then the best relays change quickly. Therefore, a small value of C would lead to frequent use of wrong best relays. Thus, the value of C should be big in that case.

In the first embodiment, all nodes on the body can combine a BCC unit 102 and a RF unit 104. All communications between two nodes on the body may be made with BCC. When a node wants to communicate with another node outside the body, it can use first its own RF unit 104. If the communication fails, then it may send the data to another node on the body via BCC. The other node can then try to forward the data with its own RF unit 104. If the communication fails, the previous step may repeat until the communication is successful or all nodes on the body failed (e.g. no node has line-of-sight). A node that initiated the communication can get a feedback from a node that was successful in forwarding the data to the node outside the body. The node that initiated the communication may learn after some time which is the best node for communication with a specific node outside of the body and can then directly send data to this node via BCC.

The above procedure provides the following advantages:
Very low latency: because a node always tries first to transmit with RF, it has little delay to put packets on the channel. If a node has never line-of-sight, it learns which is the ideal relay for a communication and transmits directly via BCC to it.
All communications on the body are processed with BCC, which saves a considerable amount of energy.
Very dynamic: if the user is moving, the fact that a node sends first via RF and then tries to find a relay enables to quickly react to new RF neighbours. If the user is not moving, the system learns the best configuration to adopt.
The procedure does not rely on any metric for finding the best relay to a node outside the body. Because metrics like measured received power vary a lot, the procedure enables a more reliable knowledge of the state of the network.

FIG. 10 shows a schematic block diagram illustrating an exemplary arrangement of a device 200 according to a second embodiment. The device 200 may be some kind of sensor platform or sensor device, even if no sensors have to be attached to it. It can comprise a body-coupled communication (BCC) unit 102, a radio frequency (RF) communication unit 104, a first sensor unit 106, a second sensor unit 108, a power supply 110, a processor or processing unit 112, a determining unit 114, a memory or storing unit 116, a modifying unit 118, and a comparing unit 120. These components are denoted by the same reference numerals as those shown in FIG. 1 and described with reference to the same. They may basically have the same or similar functionalities as the components of the device 100 shown in FIG. 1. All or part of them may be integrated into a microcontroller 122 or other component as described in connection with the first embodiment. Other modifications described in connection with the first embodiment are also applicable.

The storing unit 116 can store various information such as a first list 124 of devices in a BCC network including the device 200. In addition, it may store a second list 126 indicating for each possible destination which device provides a best radio frequency link quality. These lists 124, 126 are described in more detail below. In the following, the first list 124 may be called "on-body table", and the second list 126 can be called "off-body table". A plurality of devices 200 may form a BCC network. Such network can also include a body-worn hub device such as e.g. a RF hub device, that provides body-worn devices with wireless connectivity to a wireless local area network (WLAN infrastructure) with access points. The hub device may comprise a mid range RF transceiver conforming e.g. to IEEE 802.11 and a BCC transceiver.

Each device 200 in the BCC network may maintain a respective first list 124 (see Table 1) that lists all devices currently attached to the body along with their device type (i.e. sensor device or hub).

TABLE 1 example of first list 124

| Address of on-body device | Hub? | Time stamp of last received announcement |
| --- | --- | --- |
| 0 | Yes | 2008-05-13 08:25:10 |
| 1 | No | 2008-05-13 08:26:22 |
| 2 | No | 2008-05-13 08:23:30 |

To keep the first list 124 up-to-date, each body-worn device 200 can regularly (e.g. every minute) broadcast via BCC, i.e. by means of its respective BCC unit 102, a presence announcement containing its address and whether or not it is a hub. All devices 200 receiving such a presence announcement by their respective BCC unit 102 may update their respective first list 124 with the received information plus a time stamp of the current time. All devices 200 can regularly remove devices with outdated entries from the first list 124, i.e. entries with time stamps older than a defined first maximum expiration time (e.g. 2 minutes). That is, the processing unit 112 of a device 200 may update an entry for another device 200 in the first list 124 with a time stamp of the current time and contents of a message from the other device 200 indicating the address of the other device 200 and whether it is a hub. Further, the processing unit 112 can remove entries with time stamps older than the first maximum expiration time from the first list 124.

Each device 200 in the BCC network may maintain a respective second list 126 (see Table 2) that indicates for each off-body device the on-body device with the currently best short range RF link quality.

TABLE 2 example of second list 126

| Address of off-body device | On-body device with best LQI | Time stamp of last received LQI report |
| --- | --- | --- |
| 3 | 2 (LQI: 90%) | 2008-05-13 08:25:13 |
| 4 | 1 (LQI: 80%) | 2008-05-13 08:26:24 |
| 5 | 2 (LQI 95%) | 2008-05-13 08:23:32 |

If there is no entry in the second list 126 for an off-body device that an on-body device such as e.g. a device 200 is interested in (i.e. wants to send a message to), then the on-body device can loop through the first list 124 and ask all on-body devices via BCC, i.e. by means of its BCC unit 102, to report their link quality indication (LQI) for that off-body device. That is, the processing unit 112 of the on-body device may instruct each on-body device from the first list 124 to report its respective RF LQI associated with the off-body device. Further, the LQI of the asking on-body device itself can be determined.

To determine the LQI for the off-body device in question, the on-body devices asked may send a ping message via short range RF, i.e. by means of the respective RF communication unit 104, to that off-body device. Then, the respective resulting LQI can be reported via BCC, i.e. by means of the respective BCC unit 102. That is, each of the on-body devices asked may receive by its respective BCC unit 102 an instruction to report a RF LQI associated with it and the off-body device. The respective RF communication unit 104 can transmit a message to the off-body device and receive a response to the message from the off-body device. The respective processing unit 112 may report by the respective BCC unit 102 a RF LQI resulting from the response to the message, which can be done in dependence on a value of the LQI. That is, a determined LQI may only be reported if it exceeds a specified threshold (e.g. LQI>50%, where an LQI of 100% means best possible link quality).

All devices receiving such an LQI report can update their respective second list 126 with the received information (i.e. keeping for the given off-body device the on-body device reporting the greatest LQI) plus a time stamp of the current time. All devices may regularly remove off-body devices with outdated entries from the second list 126, i.e. entries with time stamps older than a defined second maximum expiration time (e.g. 2 minutes) that may be identical with the first maximum expiration time or differ from the same. That is, a BCC unit 102 of a device 200 can receive a RF LQI associated with another device 200 and the given off-body device. If no entry for the off-body device exists in the second list 126 stored in the storing unit 116 of the device 200, the processing unit 112 of the device 200 may store the received LQI, the address of the other device 200 and a time stamp of the current time in the second list 126. If the received RF LQI is greater than an already stored RF LQI for the off-body device, the processing unit 112 of the device 200 can update an entry for the off-body device in the second list 126 with a time stamp of the current time, the received RF LQI and the address of the other device 200. Otherwise, it may update the entry only with the time stamp of the current time. Further, the processing unit 112 of the device 200 can remove entries with time stamps older than the second maximum expiration time from the second list 126.

Figure 11:
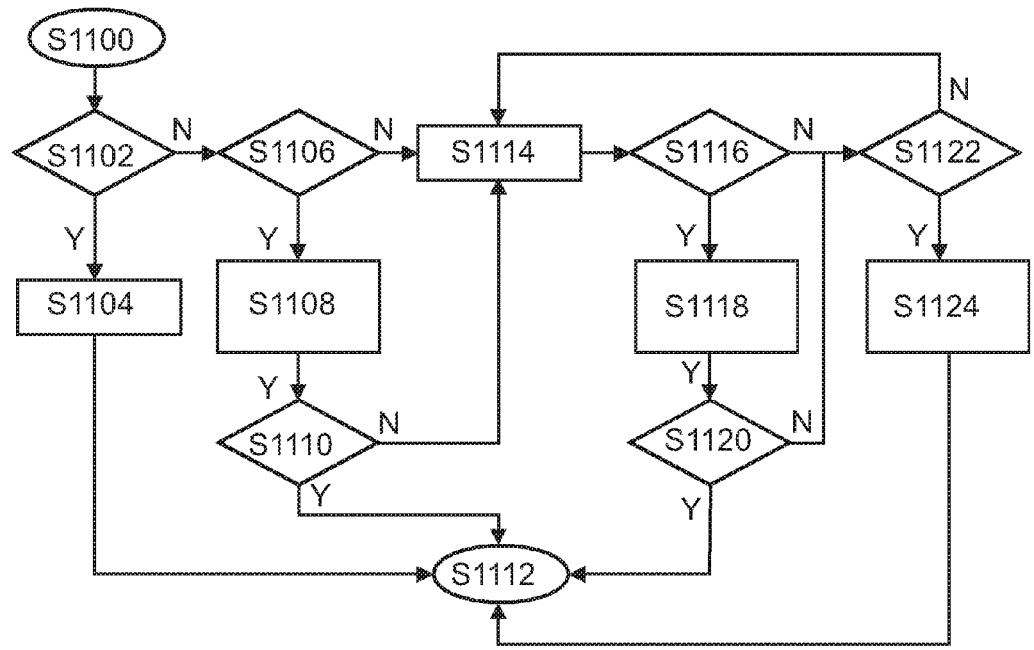
FIG. 11 shows a flowchart illustrating an exemplary procedure for on-body and off-body communication according to the second embodiment.

FIG. 11 shows a flowchart illustrating an exemplary procedure for on-body and off-body communication according to the second embodiment. An on-body device that wants to send a message to another device identified by its address can perform the following steps:

(1) After starting the procedure in a step S1100, the on-body device may check in a step S1102 whether the destination is an on-body device, by inspecting the first list 124. This can be done e.g. by the processing unit 112 that can check in the first list 124 stored in the storing unit 116 whether there is an entry for the destination. If the destination is an on-body device, then in a step S1104 the message may be directly sent via BCC, i.e. by means of the BCC unit 102, to the destination (illustrated in FIG. 12).

(2) Otherwise, the on-body device can inspect the second list 126 in a step S1106 to determine whether the destination is listed in this off-body table. This may be done e.g. by the processing unit 112 that can check in the second list 126 stored in the storing unit 116 whether there is an entry for the destination. If there is an entry for the given destination, then in a step S1108 the on-body device may send the message via BCC, i.e. by means of its BCC unit 102, to the on-body device with the best reported LQI for that off-body destination, and upon reception the intermediate on-body device can forward the message via short range RF to the destination (illustrated in FIG. 13). If it is determined in a step S1110 that the transmission has been successful, then the procedure can end in a step S1112.

(3) Otherwise (and also in case it is determined in the step S1110 that the transmission has not been successful, i.e. in case of a transmission failure), the on-body device may update its second list 126 by asking or requesting in a step S1114 all (including itself) on-body devices via BCC, i.e. by means of its BCC unit 102, to report their LQI for that off-body destination. If at least one on-body device has responded with an LQI higher than a specified threshold (e.g. 50%), then the on-body device can determine in a step S1116 that the destination is listed in the off-body table, i.e. the second list 126. Then, it may send in a step S1118 the message via BCC, i.e. by means of its BCC unit 102, to the on-body device with the best reported LQI for that off-body destination, and upon reception the intermediate on-body device may forward the message via short range RF to the destination. If it is determined in a step S1120 that the transmission has been successful, then the procedure can end in the step S1112.

(4) Otherwise, the on-body device can check in a step S1122 whether there is an on-body hub device present, by inspecting the first list 124. This may be done e.g. by the processing unit 112 that can check in the first list 124 stored in the storing unit 116 whether there is an entry for a hub device. If there is a hub device present, then the on-body device can in a step S1124 send the message via BCC, i.e. by means of its BCC unit 102, to the hub device, and the hub device may forward the message via mid range RF to a nearest access point (AP) and via a backbone infrastructure to the destination (illustrated in FIG. 15). Then, the procedure can end in the step S1112.

This is exemplified for four different scenarios in FIGS. 12 to 15. In each of these scenarios the following components may be present. There can be a body-worn hub device 0 and first and second on-body devices 1, 2 respectively corresponding to the device 200 and worn by a patient. Each of the devices 1,2 may comprise a BCC unit 102 such as e.g. a BCC transceiver and a RF communication unit 104 such as e.g. a short range RF transceiver conforming to IEEE 802.15.4. A bedside monitor 3 can be connected to a patient information centre 4 via a network 5. The hub device 0 may be used to communicate with an AP 7 such as e.g. an off-body device mounted e.g. to a room ceiling and connected to the patient information centre 4 via the network 5. The hub device 0 can comprise a BCC unit 102 such as e.g. a BCC transceiver and a RF communication unit 204 such as e.g. a mid range RF transceiver conforming e.g. to IEEE 802.11. That is, it may be a RF hub device.

Figure 12:
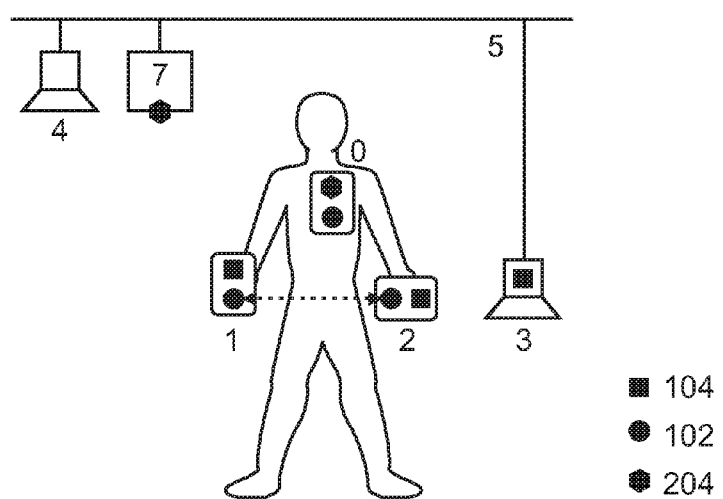
FIG. 12 illustrates a scenario where an on-body communication between devices according to the second embodiment takes place.

FIG. 12 illustrates a scenario where an on-body communication between devices 1, 2 according to the second embodiment takes place. The first on-body device 1 wants to send a message to the second on-body device 2. Since both devices are on the body, the device 1 can send the message directly via BCC to the device 2, i.e. by means of its BCC unit 102. For the scenario of FIG. 12, the following conditions may apply:

| On-body devices | Hub | Off-body devices | Best LQI |
|---|---|---|---|
| 0 | Yes | 3 | 2/90% |
| 1 | No | | |
| 2 | No | | |

Figure 13:
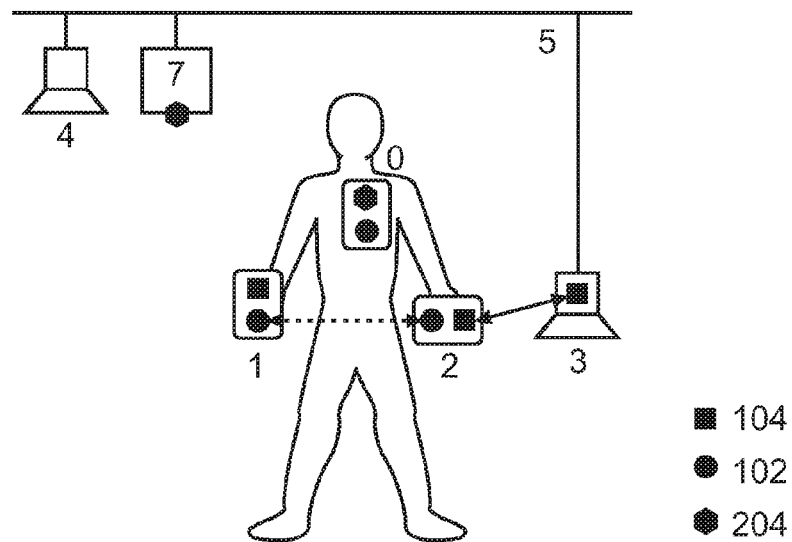
FIG. 13 illustrates a scenario where a device according to the second embodiment communicates with an off-body destination via a further device.

FIG. 13 illustrates a scenario where a device 1 according to the second embodiment communicates with an off-body destination 3 via an intermediate device 2. The device 2 currently has the best short range RF link quality to the bedside monitor 3. Therefore, the message may be sent from the device 1 via BCC, i.e. by means of its BCC unit 102, to the device 2, and in turn from the device 2 via short range RF, i.e. by means of its RF communication unit 104, to the bedside monitor 3. For the scenario of FIG. 13, the following conditions can apply:

| On-body devices | Hub | Off-body devices | Best LQI |
|---|---|---|---|
| 0 | Yes | 3 | 2/90% |
| 1 | No | | |
| 2 | No | | |

Figure 14:
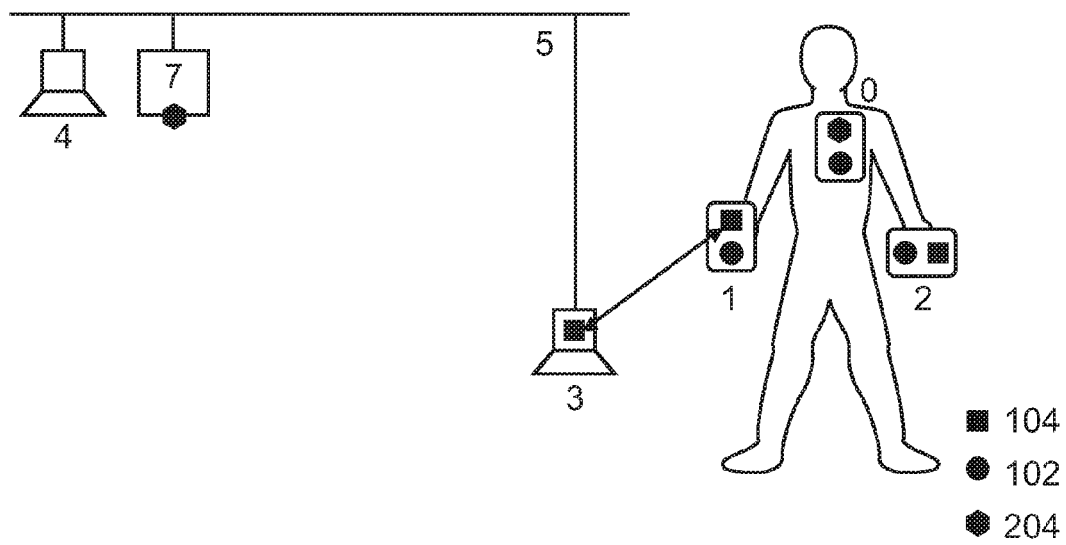
FIG. 14 illustrates a scenario where a device according to the second embodiment directly communicates with an off-body destination.

FIG. 14 illustrates a scenario where a device 1 according to the second embodiment directly communicates with an off-body destination 3. In the scenario of FIG. 14, the patient has moved. As a result, the device 1 now has the best short range RF link quality to the bedside monitor 3. Therefore, the device 1 can directly send the message via short range RF, i.e. by means of its RF communication unit 104, to the bedside monitor 3. For the scenario of FIG. 14, the following conditions may apply:

| On-body devices | Hub | Off-body devices | Best LQI |
|---|---|---|---|
| 0 | Yes | 3 | 1/95% |
| 1 | No | | |
| 2 | No | | |

Figure 15:
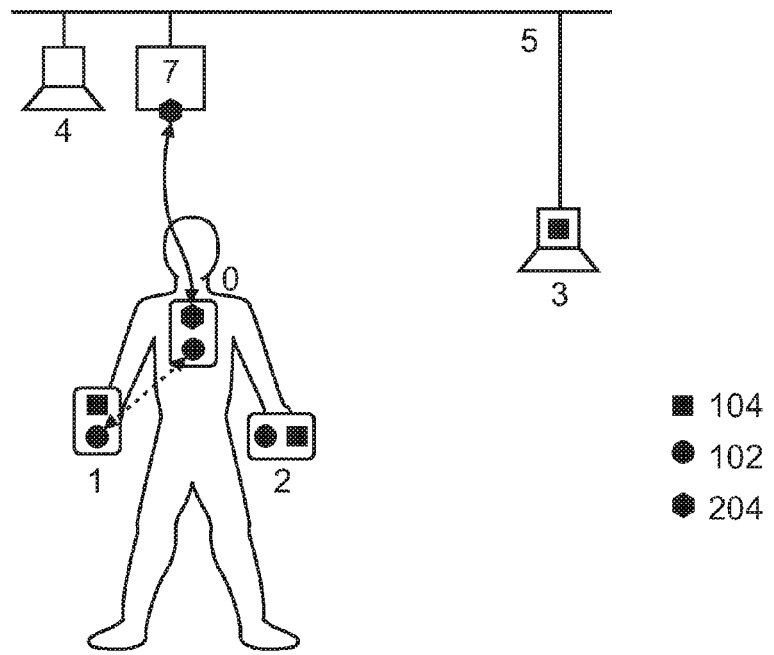
FIG. 15 illustrates a scenario where a device according to the second embodiment communicates with an off-body destination via a hub device.

FIG. 15 illustrates a scenario where a device 1 according to the second embodiment communicates with an off-body destination 3 via a hub device 0. FIG. 15 illustrates the scenario where the short range RF communication units of both devices 1, 2 are out of range of the bedside monitor 3. In this situation, the device 1 may send the message via BCC, i.e. by means of its BCC unit 102, to the hub device 0, which in turn can send the message via the WLAN infrastructure, i.e. via the AP 7 and the network 5, to the bedside monitor 3. For the scenario of FIG. 15, the following conditions may apply:

| On-body devices | Hub | Off-body devices | Best LQI |
|---|---|---|---|
| 0 | Yes | — | — |
| 1 | No | | |
| 2 | No | | |

In the second embodiment, each body-worn device can comprise both a BCC unit 102 for on-body communication and a short range RF communication unit 104 conforming to e.g. IEEE 802.15.4 for off-body communication. In addition, each device may maintain a first list 124 and a second list 126, i.e. on-body table and an off-body table.

The short range RF communication unit 104 can be used for:
- off-body communication and
- discovering all off-body devices in range and respective corresponding RF link quality indication (LQI)

The BCC unit 102 may be used for:
- on-body communication and
- discovering all on-body devices All on-body devices can exchange via BCC information about their presence and their RF link quality indications for off-body devices. They may maintain an on-body table of all on-body devices present. Further, they can maintain an off-body table indicating for each off-body device the on-body device with the best short range RF link quality to that off-body device. When an on-body source device wants to send a packet, it may determine whether or not the destination is an off-body device, by inspecting its on-body table and off-body table, respectively. If the destination is an on-body device, then the source device can send the packet directly to the destination via BCC. Otherwise, the destination is an off-body device. In this case, the source device may send the packet at first via BCC to the on-body device with the best RF link quality to the destination. The intermediate on-body device can then forward the packet via short range RF to the off-body destination. Optionally, a body-worn hub device with WLAN connectivity may be added. This can be useful for situations where all on-body devices are out of range of the destination. In this case, the source device may send the packet via BCC to the hub device, which can forward the packet via the WLAN infrastructure to the off-body destination.

Figure 16:
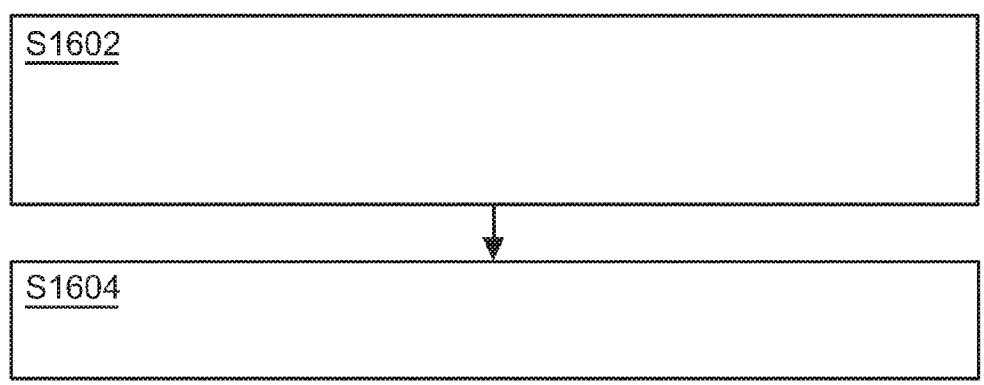
FIG. 16 shows a flowchart illustrating basic steps of an exemplary method according to the first and second embodiments.

FIG. 16 shows a flowchart illustrating basic steps of an exemplary method according to the first and second embodiments. In a step S1602, it can be decided whether data shall be transmitted by a body-coupled communication unit or a radio frequency communication unit of a device to a destination. In a step S1604 it may be decided whether the data shall be transmitted by the body-coupled communication unit to an intermediate device configured to try to transmit the data by a radio frequency communication to the destination.

Figure 17:
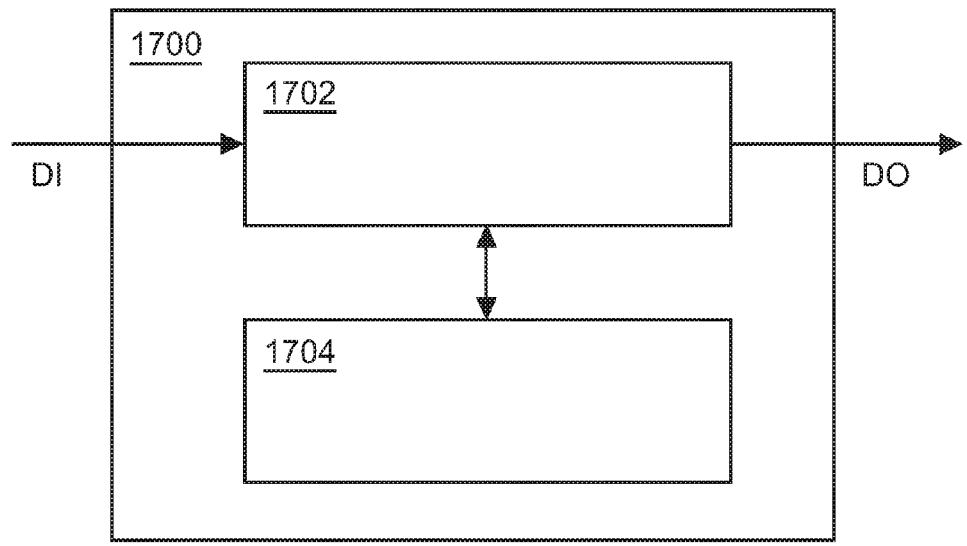
FIG. 17 shows an example of a software-based implementation of the embodiments.
Figures 18, 19:
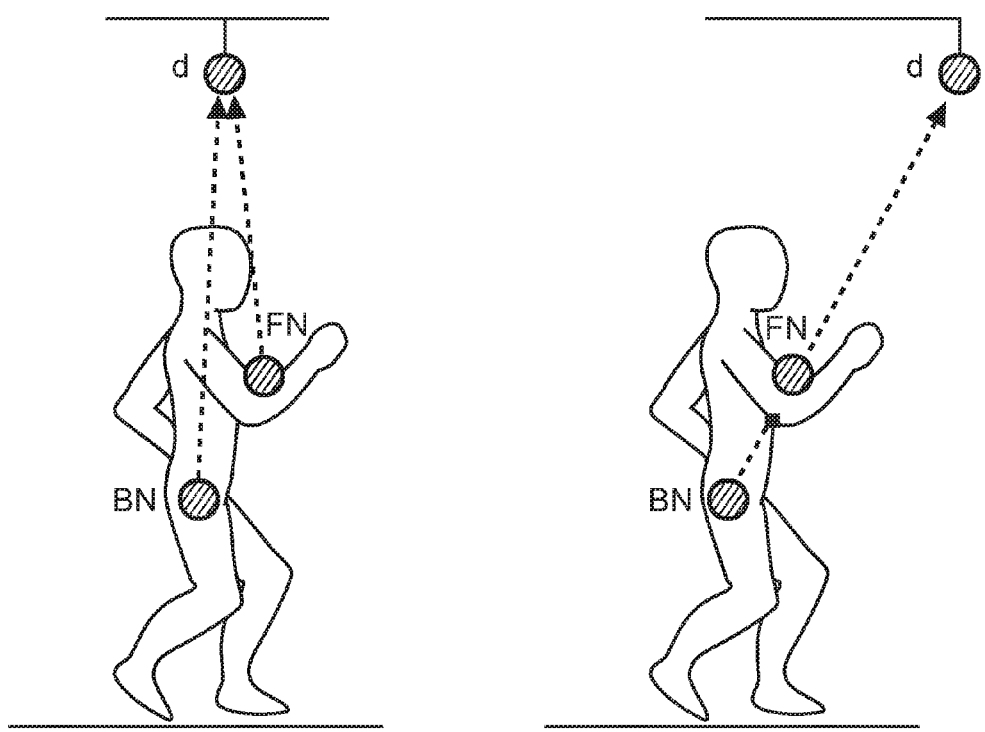
FIG. 18 illustrates a normal case of RF communication.
FIG. 19 illustrates a front case of RF communication.
Figure 20:
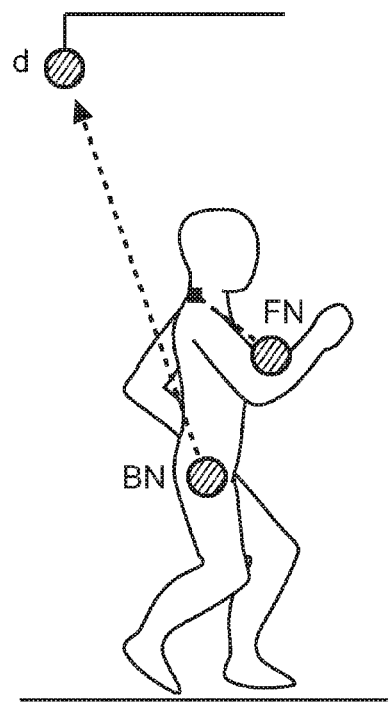
FIG. 20 illustrates a back case of RF communication.
Figure 21:
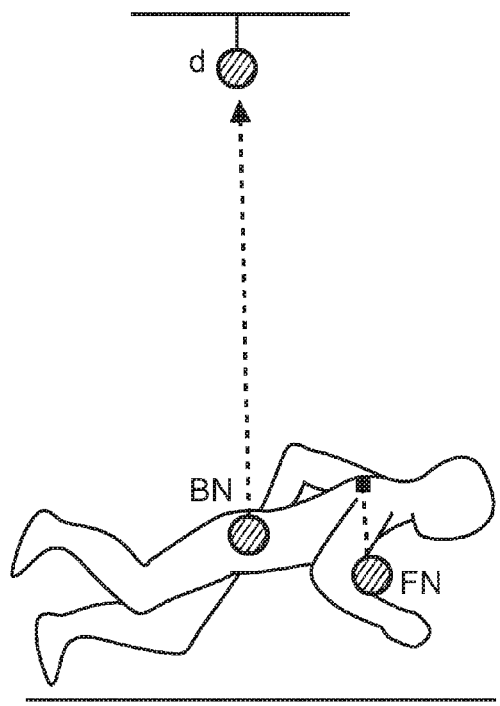
FIG. 21 illustrates a fall case of RF communication.
Figure 22:
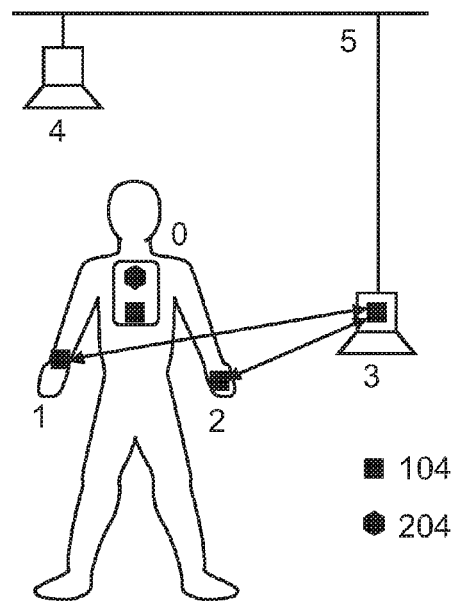
FIG. 22 illustrates an example of patient monitoring at the bedside.
Figure 23:
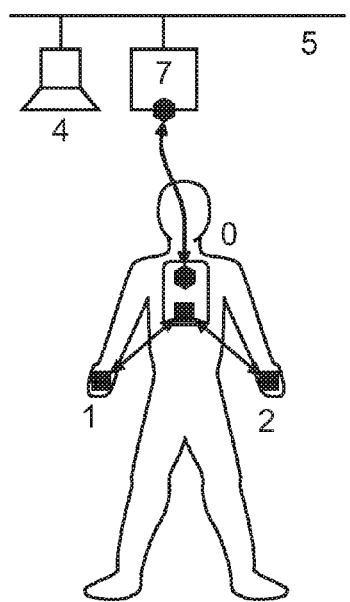
FIG. 23 shows an example of patient monitoring while a patient is ambulating.
Figure 24:
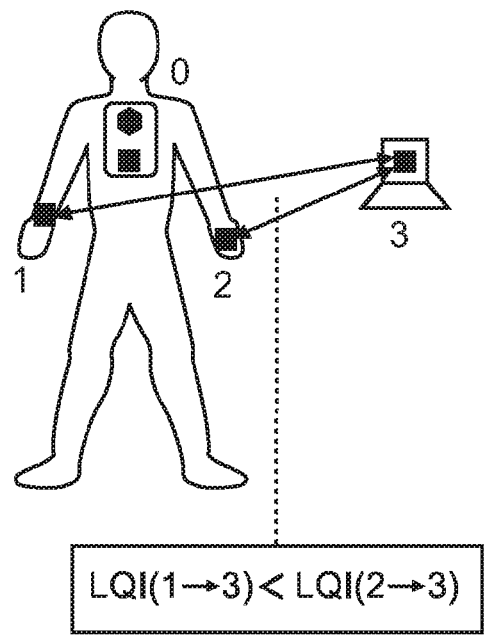
FIG. 24 illustrates a scenario where a second sensor has a better wireless link quality.
Figure 25:
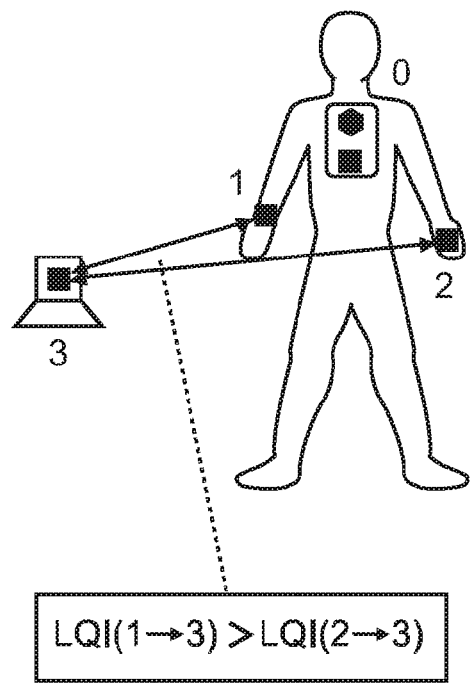
FIG. 25 illustrates a scenario where a first sensor has a better wireless link quality.

FIG. 17 shows an example of a software-based implementation of the embodiments. Here, a device 1700 can comprise a processing unit (PU) 1702, which may be provided on a single chip or a chip module and which can be any processor or computer device with a control unit that performs control based on software routines of a control program stored in a memory (MEM) 1704. Program code instructions may be fetched from the MEM 1704 and loaded into the control unit of the PU 1702 in order to perform processing steps such as those described in connection with FIGS. 11 and 16. The processing steps can be performed on the basis of input data DI and may generate output data DO. The input data DI may represent e.g. data to be communicated, information about a most suitable device for a specific destination, etc., and the output data DO can represent e.g. forwarded data, information about a source and a destination of the data, information about failed devices, etc.

The above described embodiments can be used for a plurality of applications. For example, they can be utilized for automatic fall detection (AFD) and patient monitoring in hospitals, at home and in senior living facilities. In general, they can be applied to any type of human sensing application like:

- Vital sign monitoring at home
- Consumer electronics (CE) applications (e.g. music streaming, video streaming, internet content access, etc.)
- Any application covered by IEEE 802.15.6
- Personal healthcare, wellness, and fitness applications In the above description, the abbreviation "BCC" is used to denote a body-coupled communication. However, usage of this abbreviation is not to be interpreted in any restrictive way, for example such that a specific standard is to be employed. By contrast, any kind of body-coupled communication or other body-based communication such as e.g. a communication based on bone conduction can be meant.

In summary, the present invention relates to a device, a method, a system and a computer program enabling to ensure a reliable communication even under difficult radio frequency conditions. In case data cannot be successfully communicated by a radio frequency communication, the data may be transmitted to another device by a body-coupled communication via a human or animal body. The other device can act as a relay and forward the data to an intended destination. Thus, data may be successfully transmitted to the intended destination even under difficult radio frequency conditions due to body shadowing or other effects.

While the present invention has been illustrated and described in detail in the drawings and foregoing description, such illustration and description are to be considered illustrative or exemplary and not restrictive. The invention is not limited to the disclosed embodiments.

Variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage.

A computer program capable of controlling a processor to perform the claimed features can be stored/distributed on a suitable medium, such as an optical storage medium or a solid-state medium supplied together with or as part of other hardware, but may also be distributed in other forms, such as via the Internet or other wired or wireless telecommunication systems. It can be used in conjunction with a new system, but may also be applied when updating or upgrading existing systems in order to enable them to perform the claimed features.

A computer program product for a computer can comprise software code portions for performing e.g. processing steps such as those described in connection with FIGS. 11 and 16 when the computer program product is run on the computer. The computer program product may further comprise a computer-readable medium on which the software code portions are stored, such as e.g. an optical storage medium or a solid-state medium.

Any reference signs in the claims should not be construed as limiting the scope thereof.

The invention claimed is:

1. A device comprising:
   a body-coupled communication unit configured to perform a body-coupled communication via a human or animal body;
   a radio frequency communication unit configured to perform a radio frequency communication;

a processing unit configured to decide whether data is transmitted by said body-coupled communication unit or said radio frequency communication unit to a destination, or transmitted by said body-coupled communication unit to an intermediate device configured to transmit said data by a radio frequency communication to said destination; and a determining unit configured to determine whether said data has been successfully transmitted to said destination, wherein said processing unit is configured to decide to which intermediate device said data is transmitted by said body-coupled communication unit, if a determination by said determining unit is negative.

2. The device according to claim 1, wherein said processing unit is configured to decide to which intermediate device said data is transmitted by said body-coupled communication unit.

3. The device according to claim 1, comprising a storing unit configured to store a first list of other devices in a body-coupled communication network comprising said device.

4. The device according to claim 3,
wherein said processing unit is configured to decide:
to transmit said data by said body-coupled communication unit to said destination, if said destination is present in said first list, or
to transmit said data to said destination by said radio frequency communication unit, if said destination is not present in said first list, or
to randomly select said intermediate device from said first list, excluding a source of said data and devices that already failed to successfully transmit said data by their respective radio frequency communication unit.

5. The device according to claim 3, wherein said storing unit is configured to store for each possible destination, that is not present in said first list, a respective most successful device, that is present in said first list, and a number of successful radio frequency communications of said most successful device.

6. The device according to claim 5, wherein said processing unit is configured to decide to transmit said data to a most successful device stored in said storing unit for said destination.

7. The device according to claim 5, comprising:
the determining unit further configured to determine whether a successful radio frequency communication with said destination has been performed by said radio frequency communication unit; and
a modifying unit configured to modify contents of said storing unit,
wherein said body-coupled communication unit is configured to receive an indication that a successful radio frequency communication with said destination has been performed by a radio frequency communication unit of said intermediate device, and
wherein said modifying unit is configured to
store in said storing unit said device as a most successful device for said destination together with a number of one, if said determination by said determining unit is positive and no most successful device for said destination exists,
increase in said storing unit said number for said destination and said device, if said determination by said determining unit is positive and said device is already stored as a most successful device for said destination,
store in said storing unit said intermediate device as a most successful device for said destination together with a number of one, if said body-coupled communication unit receives said indication and no most successful device for said destination exists, and
increase in said storing unit said number for said destination and said intermediate device, if said body-coupled communication unit receives said indication and said intermediate device is already stored as a most successful device for said destination.

8. The device according to claim 7, comprising:
a comparing unit configured to compare a threshold value and a respective number associated with said destination and a respective device,
wherein said processing unit is configured to decide to transmit said data to a most successful device by said body-coupled communication unit, if a number associated with said destination and said most successful device is greater than said threshold value, and
wherein said processing unit is configured to decide to transmit said data by said radio frequency communication unit, if none of said numbers is greater than said threshold value.

9. The device according to claim 1,
wherein said body-coupled communication unit is configured to transmit to said intermediate device an address of a source of said data, an address of said destination and a list of addresses of devices, including an address of said device, that already failed to successfully transmit said data by their respective radio frequency communication unit.

10. The device according to claim 1,
wherein said body-coupled communication unit is configured to receive from another device an address of a source of said data, an address of said destination and a list of addresses of devices that already failed to successfully transmit said data by their respective radio frequency communication unit, and
wherein said processing unit is configured to decide to
transmit by said body-coupled communication unit to said source of said data an indication that said data has been successfully transmitted, if said determination by said determining unit is positive,
transmit by said body-coupled communication unit to said source of said data an indication that said data has not been successfully transmitted, if said determination by said determining unit is negative and there are no other devices than said device, said source of said data and said devices the addresses of which are contained in said list of addresses of devices, and
transmit by said body-coupled communication unit to said intermediate device said address of said source of said data, said address of said destination and said list of addresses of devices, supplemented by an address of said device, that already failed to successfully transmit said data by their respective radio frequency communication unit, if said determination by said determining unit is negative and an address of said intermediate device is neither identical to said address of said source of said data nor contained in said list of addresses of devices.

11. The device according to claim 1, wherein said body-coupled communication unit is configured to receive from another device an indication that said data has been successfully transmitted or not.

12. A method comprising:
deciding whether data is transmitted by a body-coupled communication unit or a radio frequency communication unit of a device to a destination;
deciding whether said data is transmitted by said body-coupled communication unit to an intermediate device configured to transmit said data by a radio frequency communication to said destination;
determining whether said data has been successfully transmitted to said destination; and
if said data has not been successfully transmitted to said destination, deciding to which intermediate device said data is transmitted by said body-coupled communication unit.

* * * * *